United States Patent
Takai et al.

(10) Patent No.: US 6,479,130 B1
(45) Date of Patent: *Nov. 12, 2002

(54) FLEXIBLE SHEET FOR DISPOSABLE GARMENT

(75) Inventors: Hisashi Takai, Kagawa-ken (JP); Takayuki Hisanaka, Kagawa-ken (JP); Koichi Yamaki, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/498,479

(22) Filed: Feb. 4, 2000

(30) Foreign Application Priority Data

Feb. 5, 1999 (JP) ............................................. 11-029251

(51) Int. Cl.[7] ............................. A61F 13/15; A61F 13/46
(52) U.S. Cl. .................... 428/137; 428/131; 428/132; 428/138; 604/365; 604/366; 604/383; 604/385.01; 604/385.101
(58) Field of Search ................................. 428/131, 132, 428/137, 138; 604/365, 366, 370, 371, 374, 378, 383, 385.01, 385.101

(56) References Cited

U.S. PATENT DOCUMENTS

| 4,637,819 A | * | 1/1987 | Ouellette et al. | 428/131 |
| 5,891,119 A | * | 4/1999 | Ta et al. | 604/365 |
| 6,117,524 A | * | 9/2000 | Hisanaka et al. | 428/131 |

FOREIGN PATENT DOCUMENTS

| EP | 0919212 A2 | * 6/1999 | A61F/13/15 |
| JP | 62-57551 | 3/1987 | |
| JP | 7-328061 | 12/1995 | |

* cited by examiner

*Primary Examiner*—Harold Pyon
*Assistant Examiner*—Alicia Chevalier
(74) *Attorney, Agent, or Firm*—Lowe Hauptman Gilman & Berner, LLP

(57) ABSTRACT

A flexible sheet for a disposable garment includes a plastic sheet and a fibrous assembly joined to a lower surface of the plastic sheet, the plastic sheet includes a plurality of flat zones, a plurality of slit zones, bridge zones across the slit zones and rising zones rising on the upper surface of the plastic sheet repeating rise and fall substantially in saw-tooth-shape, and component fibers of the fibrous assembly partially extend upward in the slit zones.

7 Claims, 5 Drawing Sheets

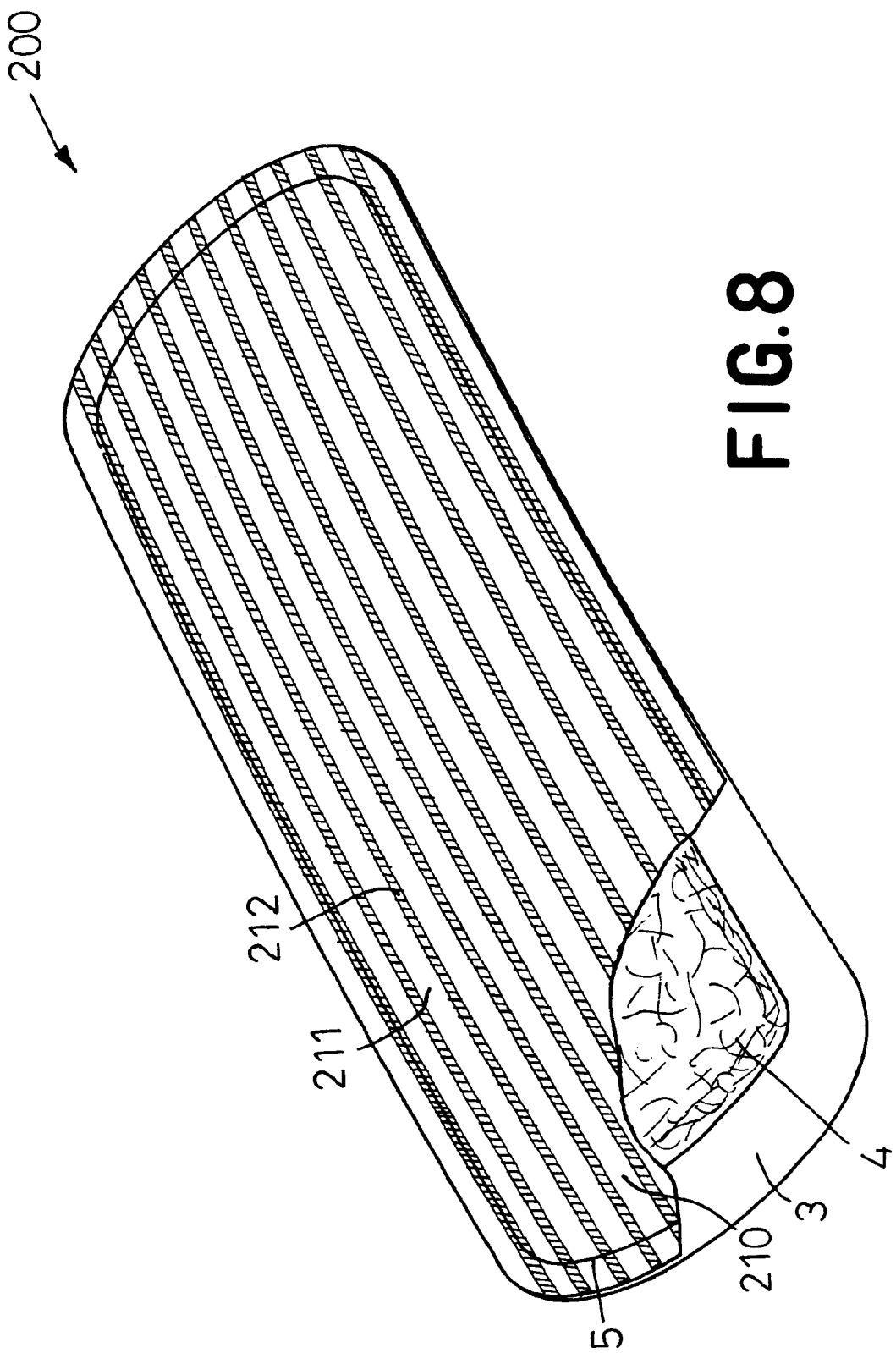

FLEXIBLE SHEET FOR DISPOSABLE GARMENT

BACKGROUND OF THE INVENTION

This invention relates to a flexible sheet suitable as stock material of disposable body fluids absorbent garment such as a disposable diaper, a urine absorbent pad or a sanitary napkin or a disposable garment such as a disposable gown used in medical facilities.

FIG. 7 of the accompanying drawings is a perspective view showing a plastic sheet 110 formed with microapertures described in Japanese Patent Application Disclosure No. 1987-57551 and claimed to offer a soft touch. The plastic sheet 110 is described to be suitable as a top- and/or backsheet of a disposable diaper and formed on its surface with a plurality of cylindrical projections 120. These projections 120 are formed, in turn, on their upper ends with microapertures 125, respectively. Such a sheet is claimed to offer a soft cloth-like touch.

FIG. 8 of the accompanying drawings is a perspective view showing a sanitary napkin 200 described in Japanese Patent Application Disclosure No. 1995-328061. In the case of the napkin, a topsheet 210 comprises a nonwoven fabric 211 and a plurality of stripe-like plastic sheets 212 bonded to the upper surface of the nonwoven fabric 211. The stripe-like plastic sheets 212 extend in parallel one to another longitudinally of the napkin 200. The nonwoven fabric 211 has its density lower in the zones defined between each pair of the adjacent plastic sheets 212, 212 than the zones underlying the respective plastic sheets 212. Menstrual discharge transfers from the low density zones toward the high density zones which are covered with the plastic sheets 212. Consequently, a stain of menstrual discharge is not remarkable, if any.

When the plastic sheet used as the topsheet and/or the backsheet of a disposable diaper or a sanitary napkin is said to offer a soft touch as the sheet comes in contact with the wearer's skin, the standard of judgement, in other words, a touch to which the touch offered by the plastic sheet is compared is generally a touch offered by a woven or nonwoven fabric made of natural or synthetic fibers or the like.

In the case of the plastic sheet described in the Japanese Patent Application Disclosure No. 1987-57551, the peripheries of the microapertures formed at the top ends of the respective cylindrical projections are broken into parts like pedals. As far as the surface of the plastic sheet is concerned, a comfortable soft touch will be obtained as the wearer's skin comes in contact with the sheet. However, a plurality of cylindrical projections formed on the plastic sheet may often be far from decreasing a rigidity of the sheet itself and rather increase the rigidity. Accordingly, it will be difficult for the known plastic sheet to obtain a softness as comfortable as the softness offered by a woven or nonwoven fabric.

The topsheet described in Japanese Patent Application Disclosure No. 1995-328061 will be able to offer a desired touch which is soft and comfortable for the wearer's skin so far as each section of the nonwoven fabric exposed between each pair of adjacent stripe-like plastic sheets is adequately large. However, if a relatively thick plastic sheet is used to form the stripe-like plastic sheets extending on the topsheet, it is concerned that respective side edges of these stripe-like plastic sheets might act like knife edges and unacceptably irritate the wearer's skin.

SUMMARY OF THE INVENTION

An object of this invention is to solve the problems inevitably encountered by the known articles as have been described above when the plastic sheet is used as one of stock materials for a body fluids absorbent garment such as a disposable diaper or a garment such as a disposable gown used in medical facilities.

According to this invention, there is provided a flexible sheet having upper and lower surfaces and adapted to be used in disposable garment.

The flexible sheet comprises a plastic sheet forming a part of the upper surface and a fibrous assembly joined to a lower surface of the plastic sheet to form the remaining part of the upper surface and entire the lower surface of the flexible sheet; the plastic sheet comprises a plurality of substantially flat zones, each having a thickness of 0.001~0.05 mm and a width of 0.03~1 mm, extending in parallel one to another in: one direction, a plurality of slit zones extending in the one direction to space each pair of the adjacent substantially flat zones from each other, bridge zones extending from mutually opposite edges of the adjacent substantially flat zones across the slit zones to connect these adjacent substantially flat zones, and rising zones rising on the upper surface of the plastic sheet repeating rise and fall substantially in saw-tooth-shape in the one direction; and the fibrous assembly comprises component fibers assembled together by mechanical intertwining, heat-sealing or adhesive bonding of the component fibers wherein the fibrous assembly contains at least one of thermoplastic synthetic fibers, chemical fibers and natural fibers and the component fibers partially extend upward in the slit zones of the plastic sheet.

This invention includes the other preferred embodiments as follow:

(1) Most of the slit zones have a width of 0.05~1 mm and a length corresponding to the width multiplied by 1.5 or larger.

(2) The bridge zones are formed along their edges with second rising zones repeating rise and fall substantially in saw-tooth-shape transversely of the one direction.

(3) The fibrous assembly contains thermoplastic synthetic fibers or chemical fibers having a fineness of 0.05~15 deniers.

(4) The fibrous assembly is formed by any one of a thermal bond nonwoven fabric, a melt blown nonwoven fabric and a spun lace nonwoven fabric.

(5) The plastic sheet is formed with a plurality of tubular zones extending from the upper surface to the lower surface and each of the tubular zones has an opening diameter of 0.1~5 mm at the upper surface of the plastic sheet.

(6) Inside the tubular zones, the component fibers partially extend upward beyond top ends of the tubular zones.

BRIEF DESCRIPTION OF THE DRAWINGS

FIG. 8 is a perspective view showing a partially cutaway sanitary napkin as another example of the prior art.

DETAILED DESCRIPTION OF THE PREFERRED EMBODIMENTS

A flexible sheet provided by this invention as one of the important stock materials for a disposable body fluids absorbent article will be described in more details with reference to the accompanying drawings.

Figure 1:
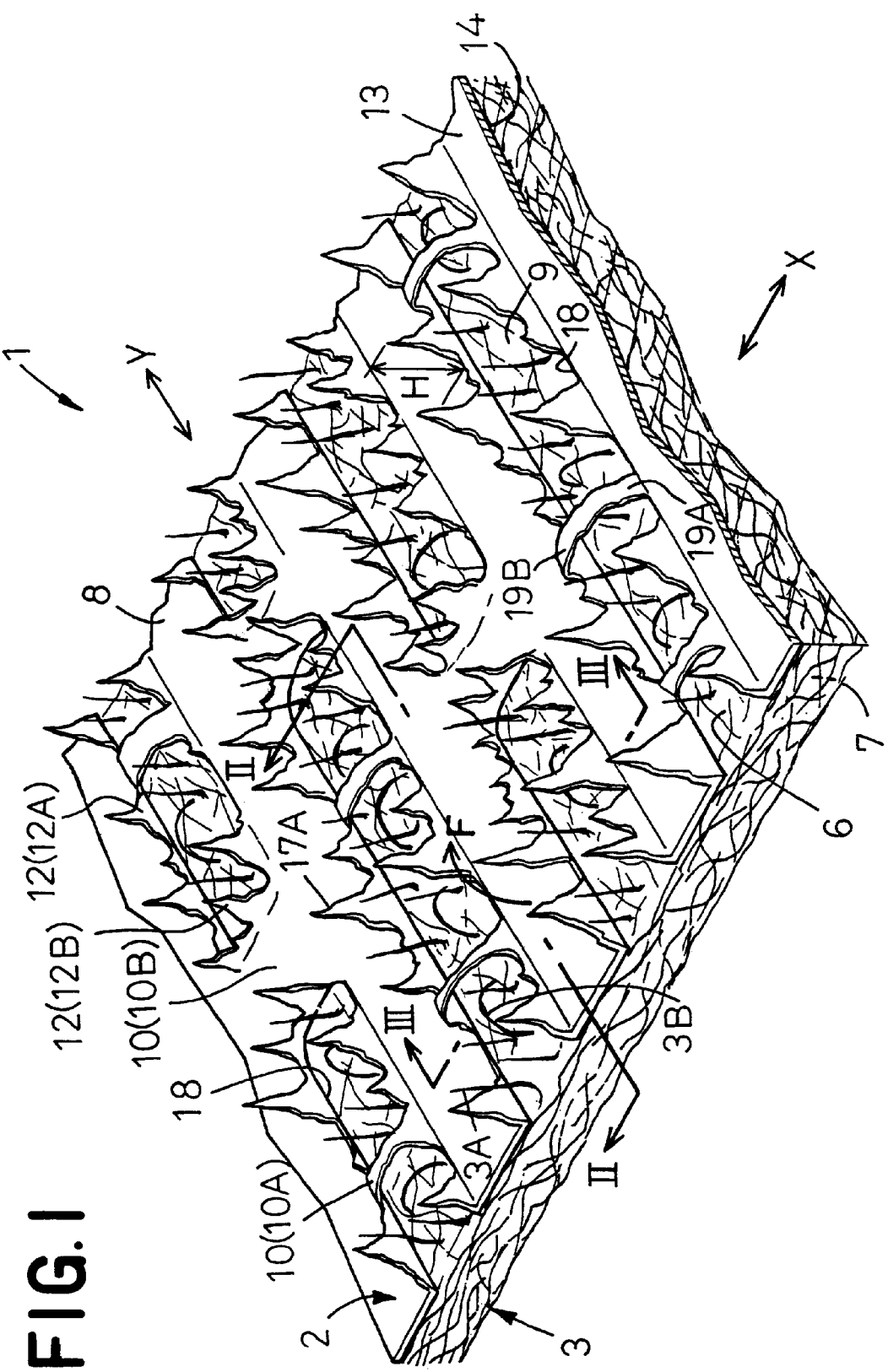
FIG. 1 is a perspective view of a typical flexible sheet according to this invention.

A flexible sheet 1 shown by FIG. 1 in a perspective view comprises a plastic sheet 2 and a fibrous assembly 3 joined to the lower surface of the plastic sheet 2. The flexible sheet 1 has its upper surface formed by the plastic sheet 2 and the fibrous assembly 3 and the lower surface formed by the fibrous assembly 3 alone.

The plastic sheet 2 is of a flexible and configured to have zones as follow: a plurality of substantially flat zones 8 extending in parallel one to another in a direction as indicated by a double-headed arrow Y; a plurality of slit zones 9 each defined between a pair of the adjacent flat zones 8, 8 and extending in the direction as indicated by the arrow Y; a plurality of bridge zones 10 each extending in a direction as indicated by a double-headed arrow X across the slit 9 to connect opposite edges 18 of the pair of the adjacent flat zones 8, 8; and a plurality of rising zones 12 each extending upward from upper surface 13 of the flat zone 8 along the edge 18. Each of the rising zones 12 describes a saw-tooth wave repeating irregular rise and fall in the direction as indicated by said arrow Y.

The fibrous assembly 3 is exposed along the respective slit zones 9 in which component fibers 3A of the assembly 3 partially extend upward in a linear or arc-shaped condition.

Figure 2:
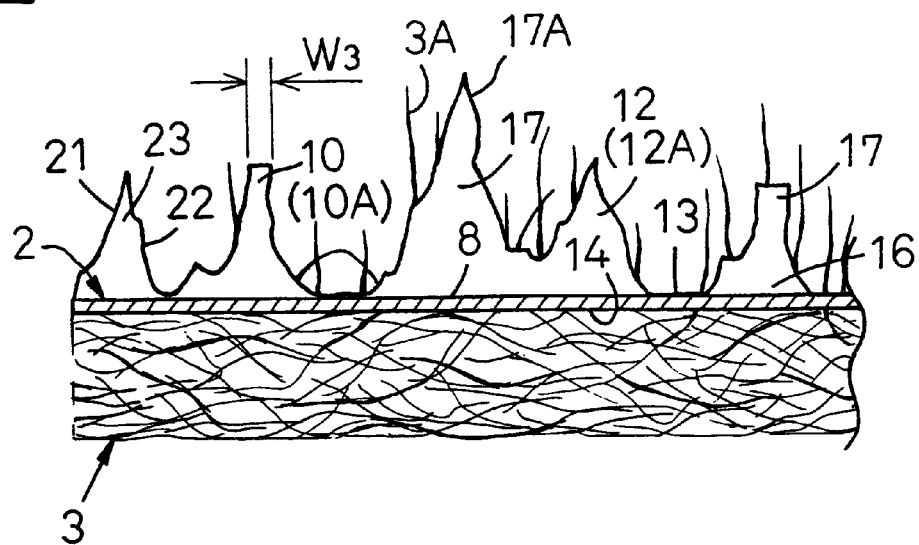
FIG. 2 is a sectional view taken along a line II—II in FIG. 1.
Figure 3:
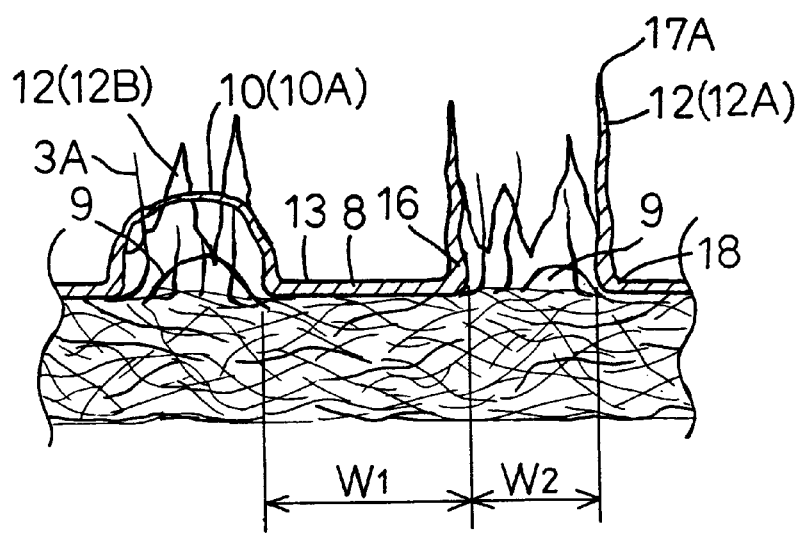
FIG. 3 is a sectional view taken along a line III—III in FIG. 1.

FIGS. 2 and 3 are sectional views taken along lines II—II and III—III in FIG. 1, respectively.

Referring to FIGS. 2 and 3, the flat zone 8 of the plastic sheet 2 has a thickness of 0.001~0.05 mm and a width $W_1$ of 0.03~1 mm as measured between each pair of the adjacent slit zones 9, 9 in the direction as indicated by the arrow X. Most of the slit zones 9 longitudinally extend in the direction as indicated by the arrow Y and each of them preferably has a width $W_2$ of 0.05~1 mm and a length corresponding to the width $W_2$ multiplied by 1.5 or larger.

The bridge zones 10 are arranged intermittently in the direction as indicated by the arrow Y comprising curved bridge zones 10A describing arcs which are upwardly convex from the upper surface 13 of the flat zones 8 and flat bridge zones 10B extending in the same plane as the flat zones 8. Some of the curved bridge zones 10A have one or both proximal end or ends 19A appearing to extend immediately from the flat zones 8 and the other have one or both proximal end or ends 19B appearing to extend from the rising zones 12 (See FIG. 1 also). Each of the bridge zones 10 preferably has a width $W_3$ of 0.001~2 mm at its narrowest region (See FIG. 2).

Rising zones 12A forming a large majority of the rising zones 12 are formed by a portion of the plastic sheet 2 extending upward from the edges 18 of the respective flat zones 8 and have proximal ends 16 being contiguous to the flat zones 8 and free ends 17 extending upward from the proximal ends 16. Upper edges 17A of the free ends 17 repeat rise and fall along the respective edges 18. A height from the upper surface 13 of the flat zones 8 to said upper edges 17A is variable in a range of 0~1 mm. Rising zones 12B forming a part of the rising zones 12 are formed along edges of the bridge zones 10 and extend in the direction as indicated by the arrow X. A height of these rising zones 12A is substantially equal to the height of the rising zones 12A (See FIG. 1 also).

An example of the manner in which the upper edge 17A of the rising zone 12A repeats rise and fall is shown by FIG. 2. As shown, such repeated rise and fall result in irregularly repeated regions 23 each presenting a triangular or a substantially triangular shape defined by a substantially rightward ascending oblique side 21, a substantially leftward ascending oblique side 22 and a proximal end 16 extending between the oblique sides 21, 22. The rising zone 12B also repeats rise and fall just like the rising zone 12A. The rising zones 12 comprising these rising zones 12A and rising zones 12B have a thickness equal to or smaller than the thickness of the flat zones 8. The rising zones 12 are flexibly deformed as they contact the wearer's skin and give the surface of the flexible sheet 1 velvet-like smooth and soft touch.

While visual recognition of the rising zones 12 is difficult, the rising zones 12 as a whole give the upper surface of the flexible sheet 1 fluffy appearance. In addition, the rising zones 12 diffusively reflect incident light and thereby prevent the upper surface 13 of the plastic sheet 2 from becoming glossy. In this manner, the rising zones 12 function to alleviate a surface gloss peculiar to the smooth plastic sheet. The surface gloss can be further alleviated by embossing the upper surface 13 of the flat zones 8 so as to form a plurality of fine irregularities. Thus, the flexible sheet 1 is substantially free from the surface gloss.

When it is intended to use such flexible sheet 1 as a liquid-pervious topsheet of a disposable diaper or a sanitary napkin, the plastic sheet 2 preferably has a breathability of 5~700 cm$^3$/cm$^2$/sec according to the prescription of JIS (Japanese Industrial Standards)-L-1096 and a water-resistance of 0~200 mm according to the prescription of JIS-L-1092. For example, a hydrophobic or hydrophilic thermoplastic sheet, or a hydrophobic thermoplastic sheet subjected to a suitable hydrophiling treatment may be used as the plastic sheet 2.

Stock material for the fibrous assembly 3 may be selected from a group consisting of thermoplastic synthetic fibers, chemical fibers such as rayon fibers, a mixture of these synthetic fibers and chemical fibers and a mixture of the synthetic fibers or the chemical fibers and natural fibers such as cotton fibers or pulp fibers. The stock material preferably has a basis weight of 2~50 g/m$^2$ and is of flexible nature. More preferably, a nonwoven fabric is used, in which the individual fibers of the synthetic, chemical or natural fibers of the mixture are mechanically intertwined and joined by heat-sealing or adhesion. An example of the preferred nonwoven fabrics comprises thermoplastic synthetic fibers or chemical fibers having a fineness of 0.05~15 deniers. The nonwoven fabric comprising thermoplastic synthetic fiber may be selected from a group consisting of a thermal bond nonwoven fabric such as a spun bond nonwoven fabric, a point bond nonwoven fabric or an air-through nonwoven fabric; a melt blown nonwoven fabric and a spun lace nonwoven fabric. When it is intended to use such fibrous assembly 3 as the liquid-pervious topsheet material, the fibrous assembly 3 preferably a breathability in the direction of its thickness in a range of 5~700 cm$^3$/cm$^2$/sec according to the prescription of JIS-L-1096 and a water-resistance in the direction of its thickness in a range of 0~200 mm according to the prescription of JIS-L-1092. The fibrous assembly 3 and the plastic sheet 2 may be bonded together by heat- or supersonic-sealing or by using suitable adhesive agent such as hot melt adhesive agent.

As will be apparent from FIGS. 1~3, the component fibers 3A of the fibrous assembly 3 being exposed along the slit zones 9 partially extend upward beyond the flat zones 8 of the plastic sheet 2 in linear or arc-shaped condition and these component fibers 3A lie between each pair of the rising zones 12 which are opposed across the slit zone 9. Most of these component fibers 3A extending upward have a height variable in a range of 0.02~5 mm, preferably in a range of 0.05~1 mm above the upper surface 13 of the flat zones 8. None of these component fibers 13A extends upward beyond the top ends of the respective rising zones 12. The component fibers 13A extending upward are effective to give the surface of the flexible sheet 1 the velvet touch even though they are not so effective as the rising zones 12 of the plastic sheet 2. In addition to this effect, the component fibers 13A extending upward are effective to prevent the rising zones 12 from collapsing and closing the slit zones 9 by contacting and supporting, from below, the rising zones 9 tending to collapse and close the slit zones 9. None of the fibers 3A extend upward beyond the top ends of the rising zones 12 and therefore it is hot concerned that these fibers might degrade the velvet touch to be offered by the rising zones 12. The bridge zones 10 connect the flat zones 8 one to another so that, even if the flat zones 8 are partially separated from the fibrous assembly 3, these parts of the flat zones 8 can be held on the surface of the fibrous assembly 3. The arc-shaped bridge zones 10A of the bridge zones 10 are effective to improve a cushioning effect expected for the surface of the flexible sheet 1. Of the bridge zones 12, the bridge zones 19B apparently extending from the top ends of the rising zones 12 are effective to prevent the rising zones 12 lying in the vicinity of these bridge zones 19B from collapsing toward the slit zones 9 or collapsing away from the slit zones 9.

The flexible sheet 1 obtained in this manner meets the demand for a sheet having a comfortable velvet touch, a breathable sheet having a comfortable touch or a breathable and liquid-pervious sheet having a comfortable touch, depending on the particular purpose for which the flexible sheet 1 is used. From the viewpoint of these properties, the flexible sheet 1 is useful not only as the liquid-pervious topsheet but also as the backsheet of the disposable body fluids absorbent article. The flexible sheet 1 is suitable also as the stock material for the disposable garment such as disposable gown used in the medical facilities. The comfortable touch of the flexible sheet 1 is derived, for the most part, from a flexibility of the plastic sheet 2 as well as the rising zones 12 thereof and a flexibility of the component fibers 3A of the fibrous assembly 3 extending upward. The breathability of the flexible sheet 1 is derived from the slit zones 9 of the plastic sheet 2 and the interstice defined by the individual fibers in the fibrous assembly 3. The liquid-permeability of the flexible sheet 1 is also derived from said slit zones 9 and said interstice. It should be understood here that the liquid-permeability largely depends on whether the plastic sheet 2 and the fibrous assembly 3 are hydrophilic or not. For example, the hydrophilic rising zones 12 of the plastic film 2 will facilitate body fluids discharged on the article to flow toward the slit zones 9. The amount of body fluids collected in the respective slit zones 9 will be then promoted under a capillary action to transfer downward when the component fibers of the fibrous assembly 3 are at least partially hydrophilic. Particularly when the fibers 3A extending upward in the respective slit zones 9 is hydrophilic, the amount of body fluids will smoothly transfer downward through the slit zones 9 even if the rising zones 9 themselves are not hydrophilic. When the fibrous assembly 3 comprises hydrophilic component fibers and contains hydrophobic component fibers by 3~30% by weight, the hydrophobic component fibers may sometimes promote the amount of body fluids to transfer downward. When the flexible sheet 1 is used as the stock material for which no liquid-permeability is required, it is not important for the plastic sheet 2 as well as the fibrous assembly 3 whether they are hydrophilic or hydrophobic.

When the flexible sheet 1 is used as the liquid-pervious topsheet of the body fluids absorbent article, body fluids discharged on the article flow on the flat zones 8 between each pair of the adjacent rising zones 12, 12 into the slit zones 9 as indicated by an arrow F (See FIG. 1) then flow through the interstice of the fibrous assembly 3 and are absorbed by the core.

Figure 4:
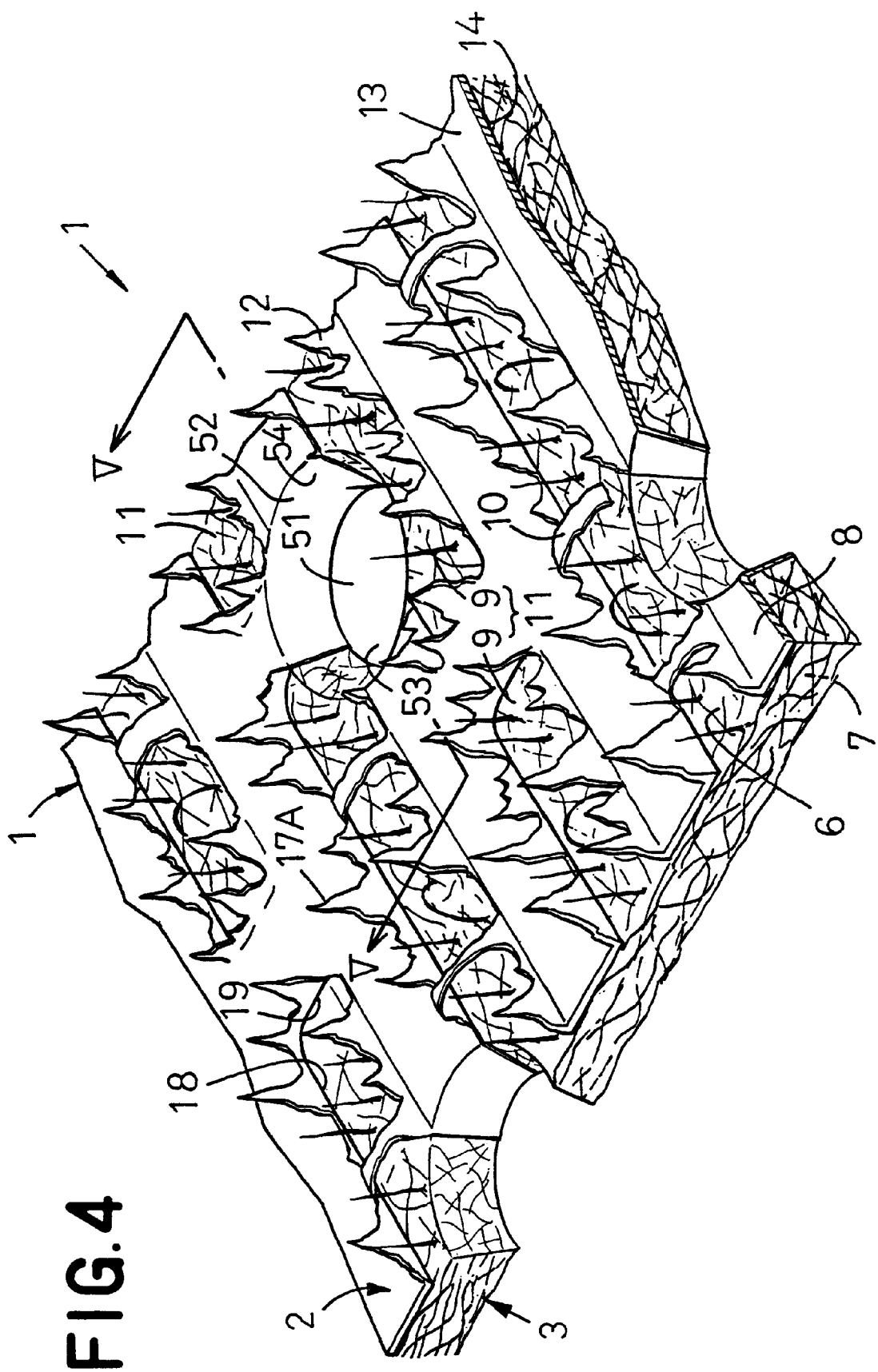
FIG. 4 is a view similar to FIG. 1 showing one preferred embodiment of this invention.
Figure 5:
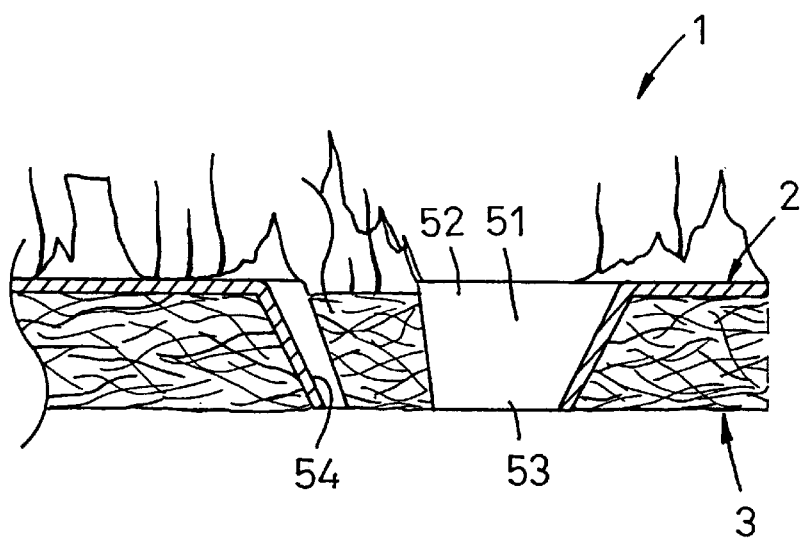
FIG. 5 is a sectional view taken along a line V—V in FIG. 4.

FIG. 4 is a view similar to FIG. 1 showing one preferred embodiment of this invention and FIG. 5 is a sectional view taken along a line V—V in FIG. 4. The flexible sheet 1 according to this embodiment is formed with a plurality of tubular zones 51 extending from the upper surface to the lower surface of the sheet 1. Each of the tubular zones 51 has an upper opening 52, a lower opening 53 and a tubular wall 54 extending between the upper and lower openings 52, 53. Each of the openings 52, 53 has a diameter preferably of 0.1~5 mm, more preferably of 1.5~5 mm, and an occupation percentage of the upper openings 52 over the upper surface of the flexible sheet 1 is preferably in a range of 1~70% more preferably in a range of 5~50%. The tubular wall 54 is tapered at an angle of 0~70° with respect to the vertical direction so that the lower opening 53 is smaller than the upper opening 52. A length of the tubular zone 51 as measured in the vertical direction is preferably in a range of 0.1~5 mm, more preferably in a range of 0.2~3 mm. The lower openings 53 are completely free from the fibrous assembly 3 and, when the flexible sheet 1 is used as the liquid-pervious topsheet of the disposable diaper, the lower openings 53 lie on the upper surface of the absorbent core.

Figure 6:
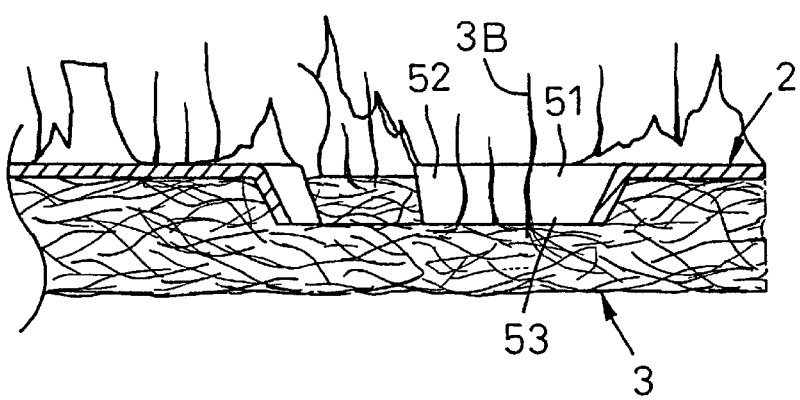
FIG. 6 is a view similar to FIG. 5 showing another preferred embodiment of this invention.
Figure 7:
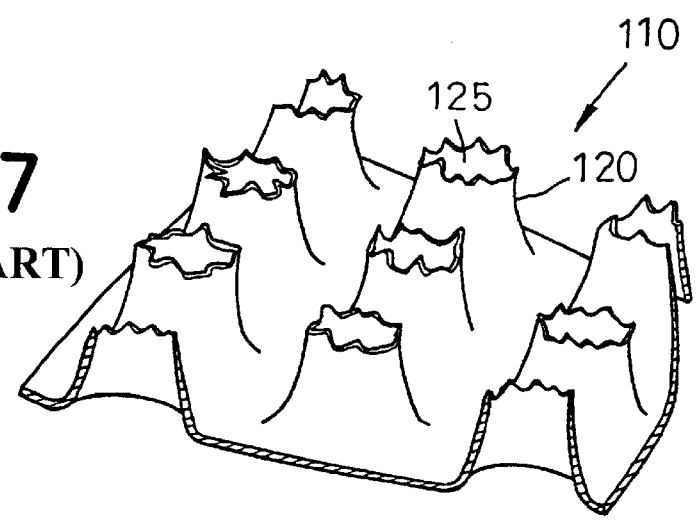
FIG. 7 is a perspective view of a plastic sheet as an example of the prior art.

FIG. 6 is a view similar to FIG. 5 showing another preferred embodiment of this invention. In the case of the flexible sheet 1 according to this embodiment, the lower openings 53 of the respective tubular zones 51 are covered with the fibrous assembly 3 and the fibrous assembly 3 is exposed inside the respective lower openings 53. The component fibers 3B of the fibrous assembly 3 in these exposed areas partially extend upward beyond the upper openings 52 and thereby contribute, just like the component fibers 3A in the previously described embodiment, to the comfortably soft touch desired for the flexible sheet 1. When the component fibers 3B are hydrophilic, they will facilitate the amount of body fluids discharged on the article to be guided under a capillary action downward along the respective tubular zones 51. This effect of guiding the body fluids will be further improved when the tubular zones 51 are hydrophobic.

As has already been described, the flexible sheet according to this invention comprises the plastic sheet and the fibrous assembly so that the upper surface of the flexible sheet is partially formed by the plastic sheet and the remaining part of the upper surface and the entire lower surface of the flexible sheet are formed by the fibrous assembly. The plastic sheet is formed with a plurality of slit zones extending in parallel one to another in one direction and the edges of the plastic sheet extending along the slit zones: are formed with the rising zones each repeating rise and fall. Inside the respective slit zones, the component fibers of the fibrous assembly partially extend upward and prevent the rising zones from collapsing to close the slit zones. With such unique arrangement, the sufficiently collapse-resistant rising zones cooperate with the component fibers extending upward to enable the flexible sheet to maintain its comfortable soft touch. Additionally, the flexible sheet will be able to maintain its liquid-permeability for a long time when this flexible sheet is used as the liquid-pervious sheet of the body fluids absorbent article because the slit zones are not easily closed or clogged.

According to the embodiment in which the flexible sheet is formed with a plurality of tubular zones extending from the upper surface to the lower surface thereof, the component fibers of the fibrous assembly extending upward from the lower openings of the tubular zones. These component fibers improve the comfortable touch of the flexible sheet and promote the liquid-guiding function of the tubular zones.

What is claimed is:

1. A flexible sheet for a disposable garment, said flexible sheet comprising an apertured web and a fibrous layer;

said apertured web comprising a plastic web having longitudinal and transverse directions, being from about 0.001 to about 0.05 mm thick, and including
a plurality of substantially flat portions, each being from about 0.03 to about 1 mm wide, imperforated, and extending in parallel one to another in said longitudinal direction, and
a plurality of intermittent apertures extending in said longitudinal direction between said flat portions having upper and lower surfaces so as to form a plurality of aperture rows extending in parallel one to another in said longitudinal direction;

pairs of said flat portions having said aperture rows therebetween being interconnected by a plurality of bridge portions which extend therebetween and across said aperture rows;

said bridge portions extending across the respective aperture rows being formed intermittently in the transverse direction, providing two types of bridge portions: those which extend upward or downward from the upper surfaces of the flat portions to the upper surfaces of the respectively adjacent flat portions so as to describe arcs and those which are flush with the flat portions;

said intermittent apertures being defined by edges of said flat portions which extend in said longitudinal direction and edges of said bridge portions which extend in said transverse direction;, said flat portions being provided at least along said edges thereof which extend in said longitudinal direction with a first set of substantially pointed tooth-shaped portions which extend upward from the upper surfaces of said flat portions;

said fibrous layer being joined to the lower surfaces of said flat portions of said apertured web; and said fibrous layer comprising component fibers assembled together by mechanical intertwining, heat-sealing or adhesive bonding of the component fibers, wherein said fibrous layer contains at least one of thermoplastic synthetic fibers, chemical fibers and natural fibers, and at least part of said component fibers extend upwardly in said intermittent apertures of said apertured web.

2. The flexible sheet according to claim 1, wherein most of said intermittent apertures have a width of from about 0.05 to about 1 mm and a length which is about 1.5 or more times of said width.

3. The flexible sheet according to claim 1, wherein said bridge portions are provided along the edges thereof with a second set of substantially pointed tooth-shaped portions which extend upwardly and along said transverse direction.

4. The flexible sheet according to claim 1, wherein said fibrous layer contains thermoplastic synthetic fibers or chemical fibers having a fineness of from about 0.05 to about 15 deniers.

5. The flexible sheet according to claim 1, wherein said fibrous layer is formed by any one of a thermal bond nonwoven fabric, a melt blown nonwoven fabric and a spun lace nonwoven fabric.

6. The flexible sheet according to claim 1, further comprising a plurality of liquid guiding passages extending through thicknesses of said apertured web and said fibrous layer, wherein each of said liquid guiding passages has a top opening, at a level of the upper surfaces of said flat portions of said apertured web, of from about 0.1 to about 5 mm in diameter.

7. The flexible sheet according to claim 6, wherein at least part of said component fibers extend upwardly beyond the top openings of said liquid guiding passages.

* * * * *